(12) United States Patent
Hubbard

(10) Patent No.: US 7,377,686 B2
(45) Date of Patent: May 27, 2008

(54) DISPOSABLE MIXING SYSTEM

(75) Inventor: John Dana Hubbard, Billerica, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 10/819,806

(22) Filed: Apr. 7, 2004

(65) Prior Publication Data

US 2005/0063250 A1    Mar. 24, 2005

Related U.S. Application Data

(60) Provisional application No. 60/500,024, filed on Sep. 4, 2003.

(51) Int. Cl.
*B01F 13/00* (2006.01)

(52) U.S. Cl. ...................... 366/208; 366/275

(58) Field of Classification Search ............ 366/208, 366/209, 275, 341, 348, 349
See application file for complete search history.

(56) References Cited

U.S. PATENT DOCUMENTS

| 2,406,403 A | * | 8/1946 | Rogers | 526/62 |
|---|---|---|---|---|
| 3,656,716 A | * | 4/1972 | Ljungerg et al. | 366/76.1 |
| 3,819,158 A |   | 6/1974 | Sharpe et al. |   |
| 4,153,375 A | * | 5/1979 | Hillyar-Russ | 366/275 |
| 4,784,297 A |   | 11/1988 | Katz |   |
| 4,808,159 A | * | 2/1989 | Wilson | 604/6.13 |
| 6,290,669 B1 | * | 9/2001 | Zicherman | 604/29 |
| 2002/0107131 A1 | * | 8/2002 | Jorgensen et al. | 494/37 |
| 2003/0082069 A1 | * | 5/2003 | Kuzyk | 422/1 |
| 2004/0062140 A1 | * | 4/2004 | Cadogan et al. | 366/144 |

FOREIGN PATENT DOCUMENTS

| EP | 0 695 575 |   | 7/1995 |
|---|---|---|---|
| JP | 55061397 |   | 5/1980 |
| SU | 883360 B | * | 11/1981 |
| WO | WO 94/27715 |   | 12/1994 |
| WO | WO 01/83004 |   | 11/2001 |
| WO | WO 03/013713 |   | 2/2003 |

\* cited by examiner

*Primary Examiner*—David L Sorkin

(57) ABSTRACT

The present invention uses one or more bags that are capable of being selectively pressurized and deflated in conjunction with a disposable bio bag such as a fermenter, mixing bag, storage bag and the like. The pressure bag(s) may surround a selected outer portion of the bag or may be contained within an inner portion of such a bag. By selectively pressurizing and deflating the pressure bag(s), one is able to achieve fluid motion in the bag thereby ensuring cell suspension, mixing and gas transfer within the bag without damaging shear forces or foam generation.

10 Claims, 6 Drawing Sheets

DISPOSABLE MIXING SYSTEM

CROSS-REFERENCED TO RELATED APPLICATIONS

The present application claims the benefit of U.S. Provisional Patent Application No.: 60/500,024, filed on Sep. 4, 2003. The entire contents of which are incorporated in their entirety herewith.

The present invention relates to a disposable mixing system. More particularly, it relates to a system useful for mixing components or for providing agitation in the biopharmaceutical industry.

BACKGROUND

The biopharmaceutical industry has traditionally used stainless steel systems and piping in their manufacturing process as they are capable of being steam sterilized and reused.

The cost of such a system is often prohibitive. Moreover, such systems are static, often being welded together and not easily reconfigured.

The industry has begun to explore an alternative approach, namely to use plastic, single disposable bags and tubing to replace the traditional stainless steel. This allows one the flexibility to rearrange these systems at minimal cost. Additionally, the initial capital cost is several times less than that of stainless steel allowing one to manufacture biopharmaceuticals in smaller amounts, making available new therapeutic agents that prior to this advancement were not economically justified and allowing for the expansion of contract manufacturing of such products or when demand requires additional capacity quickly.

One aspect of the disposable biopharmaceutical plant has been the bioreactor, which needs a steady supply of gas and nutrients and removal of waste products and expelled gases. Additionally, a constant movement of the cells in the reactor helps to provide a constant mixing of the contents.

One system for a bioreactor has been to use a large table, equipped with motors or hydraulics onto which a bioreactor bag is placed. The motors/hydraulics rock the bag providing constant movement of the cells. Additionally, the bag has a gas and nutrient supply tube and waste gas and waste product tube which allow for the supply of nutrients and gases such as air for aerobic organisms and the removal of waste such as respired gases, carbon dioxide and the like. The tubes are arranged to work with the motion of the bag to allow for a uniform movement of the gases and fluids/solids. See U.S. Pat. No. 6,191,913.

Such a system requires the use of capital-intensive equipment, with components that are susceptible to wear. Additionally, the size of the bag that can be used with the table is limited by the size of table and the lifting capability of its motors/hydraulics.

An alternative system uses a long flexible tube-like bag that has both ends attached to movable arms such that the bag after filling is suspended downwardly from the movable arms in the shape of a U. The arms are then alternately moved upward or downward relative to the other so as to cause a rocking motion and fluid movement within the bag. If desired the mid section may contain a restriction to cause a more intimate mixing action.

This system requires the use of a specially shaped bag and hydraulic or other lifting equipment to cause the movement of the liquid. Additionally, due to weight considerations, the bag size and volume is restricted by the lifting capacity of the equipment and the strength of the bag.

What is needed is a less expensive device that is not limited by size to perform the same function as the existing devices and which eliminates or minimizes the capital expense involved in such devices. More preferably, this device is disposable.

The present invention provides such a device.

SUMMARY OF THE INVENTION

The present invention uses one or more bags that are capable of being selectively pressurized and deflated in conjunction with a disposable bio bag such as a fermenter, mixing bag, storage bag and the like. The pressure bag(s) may surround a selected outer portion of the bag or may be contained within an inner portion of such a bag. By selectively pressurizing and deflating the pressure bag(s), one is able to achieve fluid motion in the bag thereby ensuring cell suspension, mixing and/or gas and/or nutrient/excrement transfer within the bag without damaging shear forces or foam generation.

Preferably, two or more pressure bags are used at or near the opposite ends of the bag. Each pressure bag has an inlet and an outlet that can be selectively opened or closed. An air supply is provided to the inlet of the pressure bag. Optionally, a vacuum supply is provided to the outlet. As one pressure bag is inflated by closing the outlet and opening the inlet, the other is deflated by closing the inlet and opening the outlet. This inflation/deflation applies a pressure to one end of the bag compressing the fluid in that end and moving it toward the end at which the pressure is less. By alternating the inflation/deflation in the opposite pressure bags, one obtains a wave or rocking movement of the fluid throughout the bag.

IN THE DRAWINGS

DETAILED DESCRIPTION

Figure 1:
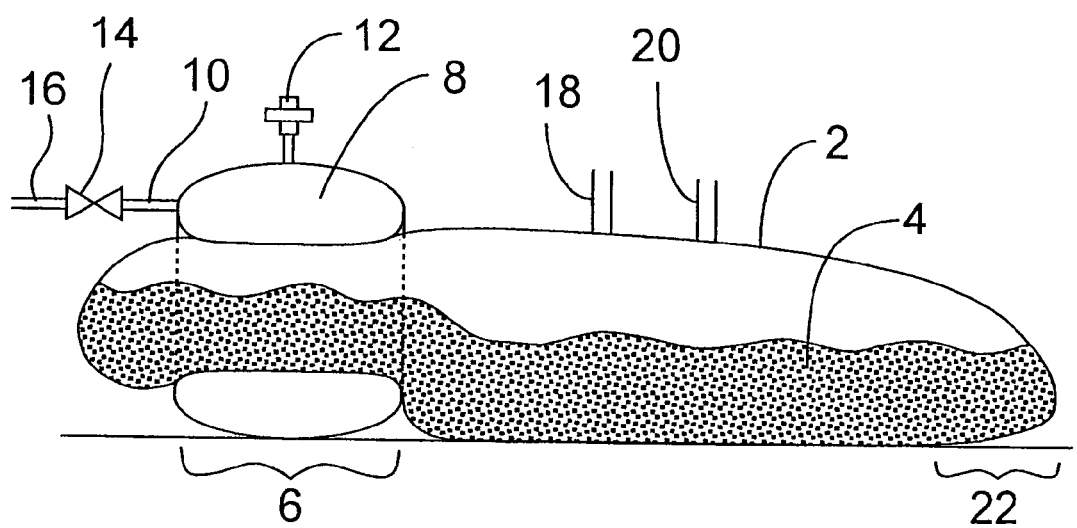
FIG. 1 shows a first embodiment of the present invention in cross-sectional view.

FIG. 1 shows a first embodiment of the present invention. It consists of a bag 2 containing a fluid 4. The fluid may be a cell suspension, a fermentation broth or some other liquid.

Positioned around a portion 6 of the bag 2 is a pressure bag 8. As shown, the pressure bag 8 is located toward one end of the bag 2. It could also be positioned near or at the middle or the other end of the bag 2 as one desires. Alternatively, and as described below the pressure bag(s) 8 may be contained within the interior of the bag 2.

The pressure bag 8 has an inlet 10 and an outlet 12. Preferably, at least the inlet 10 has a valve 14 to selectively close off the inlet 10 from a pressurizing fluid supply 16. Preferably, the pressurizing fluid supply 16 is air or some other gas although in some applications, it may be a liquid such as water or other hydraulic fluid.

The bag 2 also contains an inlet 18 and an outlet 20 which preferably are connected to either a sterile filter or a closed, sterile system (not shown).

To use the system, one opens the bag inlet 18 and introduces a liquid 4 and/or gases, such as a microbial containing liquid and nutrient supply in the case of a bioreactor. Such fluids are well known and can comprise an aqueous medium and one or more cell lines for fermentation and growth. One such fluid is an $E.\ coli$ containing fluid made from tissue cell culture medium, vitamins and other nutrient supplements. Other applications can include wine making, beer making, the mixing of large volumes of components, such as a powder into a liquid or two miscible liquids and the like. The amount of liquid introduced is typically less than the volume of the bag 2 itself. Typically from about 10 to about 90%, preferably from about 20 to about 80% of the bag 2 volume is taken up by the liquid 4. One may introduce a gas into some or all of the remaining volume as desired. In most embodiments, the volume of liquid/gas within the bag 2 shall be less than the total volume of the bag 2. In some cases, it may be equal to the remaining volume of the bag 2 to create a relatively rigid container.

The bag inlet 18 and outlet 20 may either then be closed or left open provided they are in a closed system or provided with a sterilizing grade filter (not shown) to prevent the movement of contaminants, such as bacteria or viruses into the bag 2 or the movement of constituents in the bag 2 out of the bag 2 as an aerosol or the like.

The pressure bag 8 is initially deflated. Outlet 12 is closed and inlet 10 is opened to the pressurizing fluid supply 16 through valve 14. The pressure bag 8 inflates compressing the area 6 of the bag 2 that it surrounds. This causes the fluid 4 in the bag 2 to move toward the opposite end 22 of the bag 2. When sufficient pressure is reached, the inlet valve 14 is closed and outlet 12 is opened to release the pressure, causing the fluid 4 to move back toward the area 6 containing the pressure bag 8.

Figure 2:
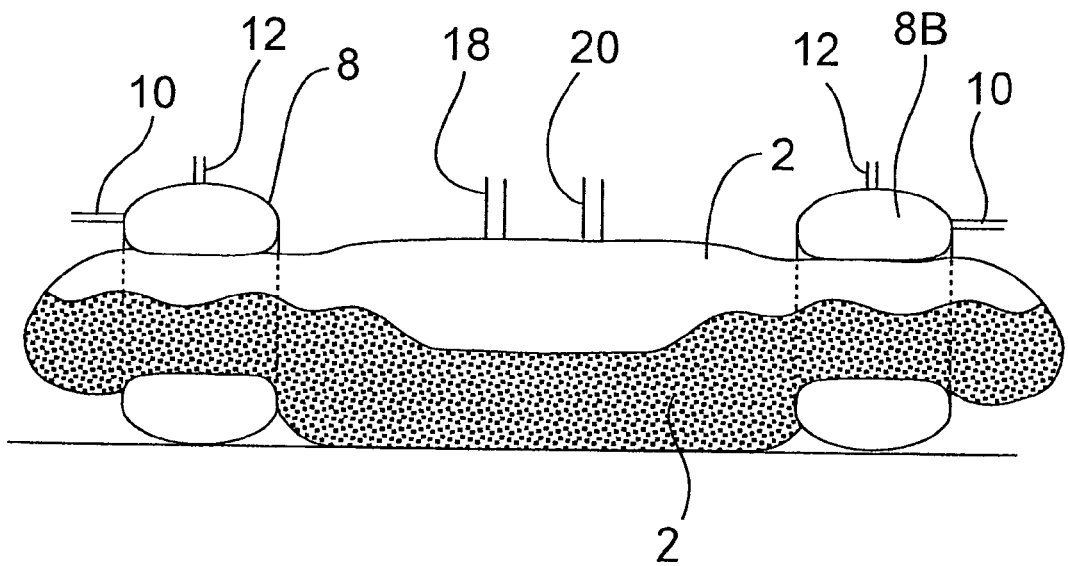
FIG. 2 shows a second embodiment of the present invention in a cross-sectional view.

FIG. 2 shows an embodiment in which two pressure bags 8A and 8B are used. They operate sequentially so that while 8A is being inflated, 8B is deflated and vice versa.

Figure 3:
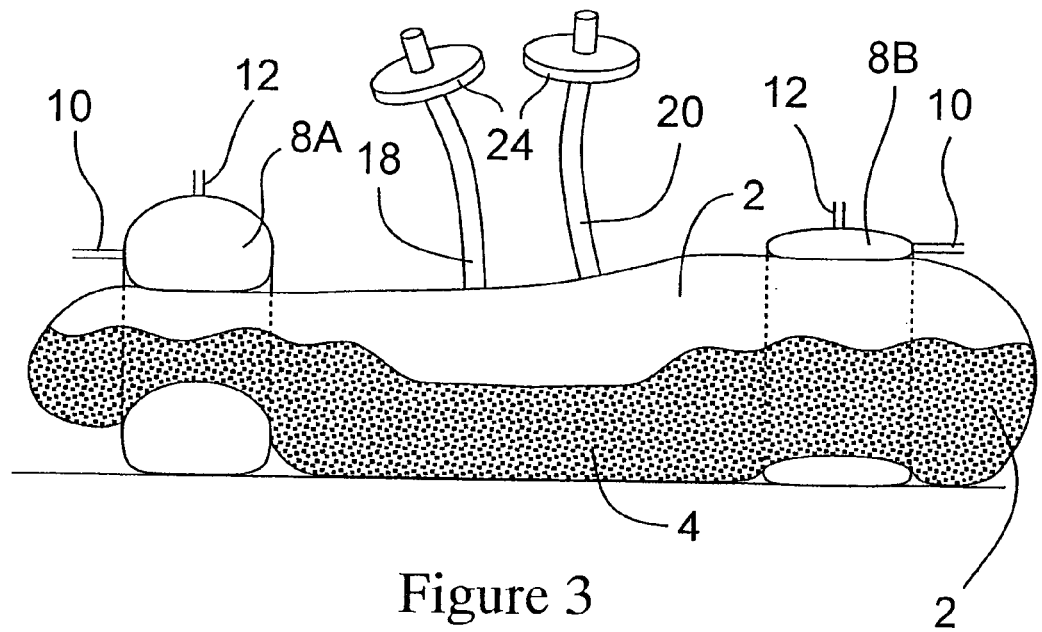
FIG. 3 shows the embodiment of FIG. 2 in use.

FIG. 3 shows the embodiment of FIG. 2 in use. Pressure bag 8A has been inflated and pressure bag 8B deflated. The liquid 4 is shown as moving to the end of the bag containing pressure bag 8B. Also shown in this Figure are the sterilizing grade filters 24 or the bag 2 inlet 18 and outlet 20.

Figure 4:
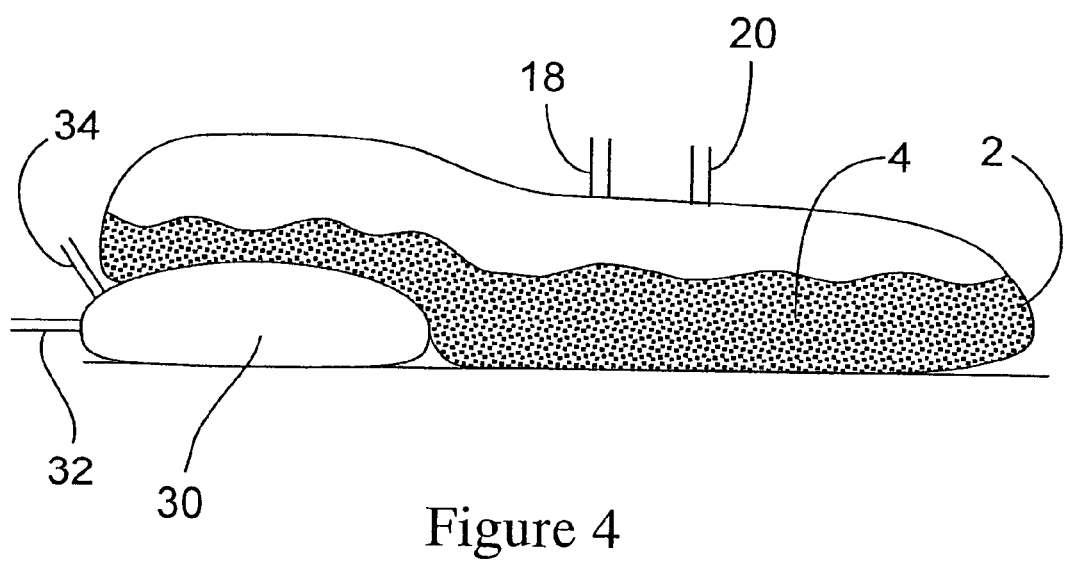
FIG. 4 shows a third embodiment of the present invention in cross-sectional view.

FIG. 4 shows another embodiment of the present invention. The pressure bag 30 is located under a portion of the bag 2. In this instance, it is shown at or near the left end of the bag 2. It may be at or near the right end or in the middle. Additional pressure bags 30 may also be used, such as having one at or near each end of the bag 2.

The inlet 32 and outlet 34 of the pressure bag 30 operate in the same manner as in FIGS. 1-3 to alternately inflate and deflate the pressure bag 30 causing the fluid 4 in the bag 2 to move.

If necessary, some means for securing the pressure bag 30 to the bag may be provided to prevent it from moving off of the bag (not shown). Straps, hook and loop attachment tapes, adhesives, heat bonding and the like may be used as the attachment means.

Figure 5:
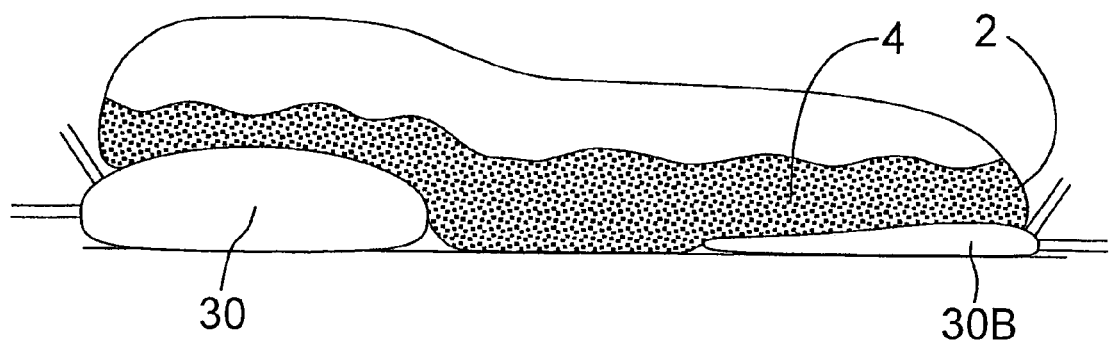
FIG. 5 shows another embodiment of the present invention in cross-sectional view.

FIG. 5 shows an embodiment of FIG. 4 using two pressure bags 30A and 30B. Bag 30A is shown as being inflated and 30B as being deflated. By alternately inflating/deflating the two bags 30A and 30B one creates a wave motion in the bag 2 and fluid 4 contained within it.

Figure 6:
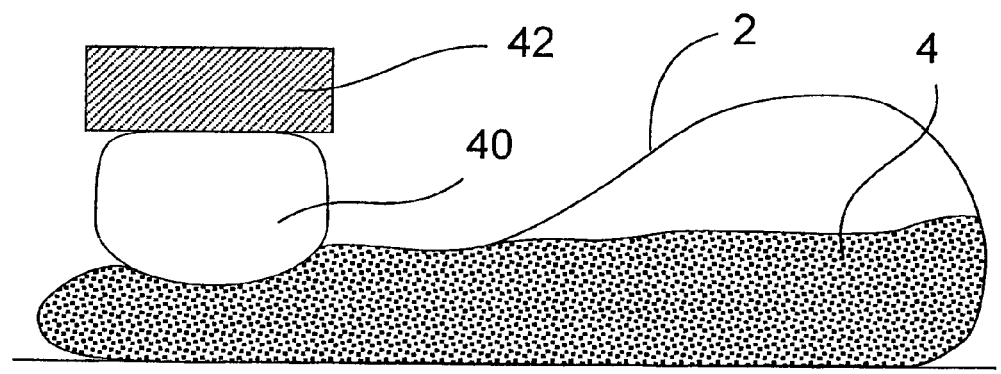
FIG. 6 shows another embodiment of the present invention in cross-sectional view.

FIG. 6 shows another embodiment in which the pressure bag 40 is located above or aside the bag 2 rather than around it or below. In this instance, the pressure bag 40 is secured to an immovable plate 42 so that all force applied to the pressure bag 40 is directed against the bag 2. Such a plate 42 can be a metal, plastic, or wooden beam or plate secured to a wall, frame or the like. As with the other embodiments above, more than one pressure bag 40 may be used in such a system, preferably at different locations along the length of the bag 2.

Figure 7:
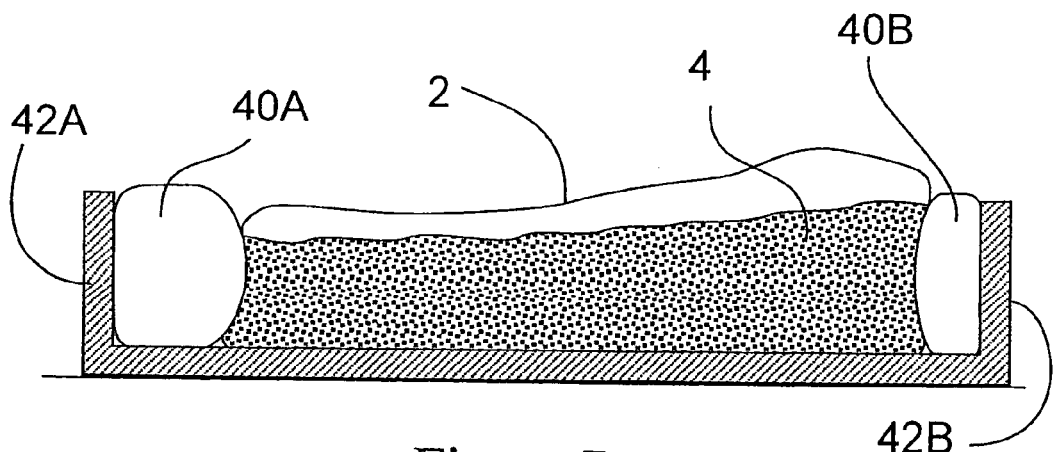
FIG. 7 shows another embodiment of the present invention in cross-sectional view.

FIG. 7 shows a variation of the embodiment of FIG. 6 in which pressure bags 40A and 40B are mounted on plates 42A and 42B respectively at the end of the bag 2. As shown, the inflation of one bag, in this instance 40A causes fluid movement toward the other end where bag 40B is deflated. Alternate inflation/deflation of the bags 40A and 40B causes the movement of the fluid 4 in the bag.

Figure 8:
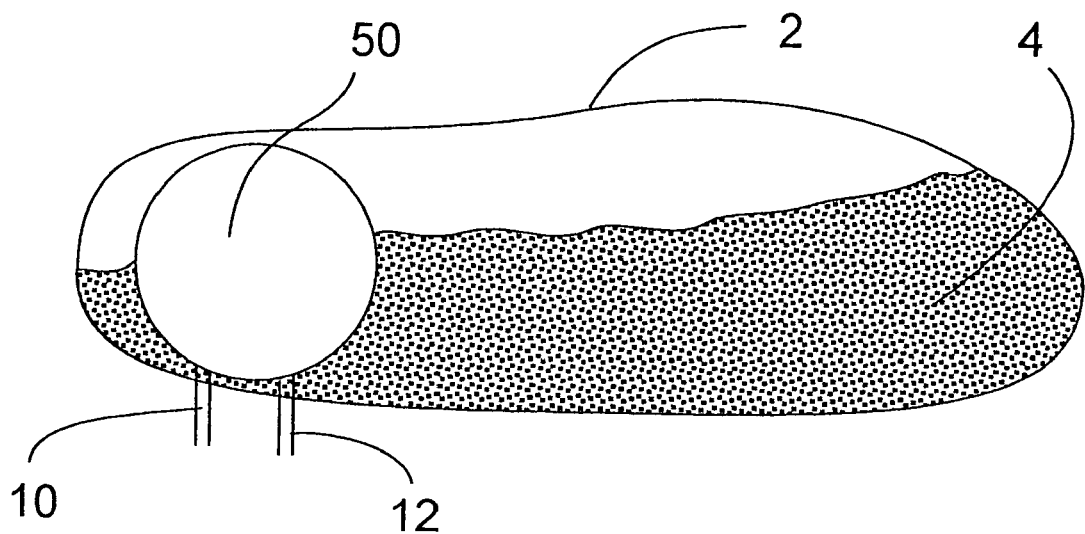
FIG. 8 shows another embodiment of the present invention in cross-sectional view.

FIG. 8 shows another embodiment of the present invention. In this embodiment, the pressure bag 50 is contained within the bag 2. Inlet and outlet 12 to the pressure bag 50 are forward through openings in the bag wall forming a liquid proof seal around the inlet 10 and outlet 12.

Figure 9:
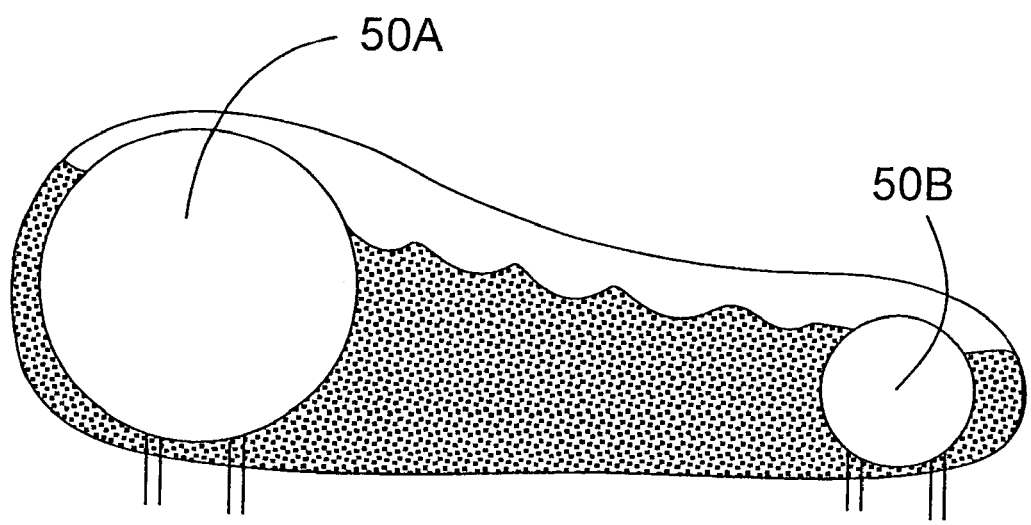
FIG. 9 shows another embodiment of the present invention in cross-sectional view.

FIG. 9 shows an embodiment with similar to that of the embodiment of FIG. 8 but having two pressure bags 50A and 50B.

Figure 10:
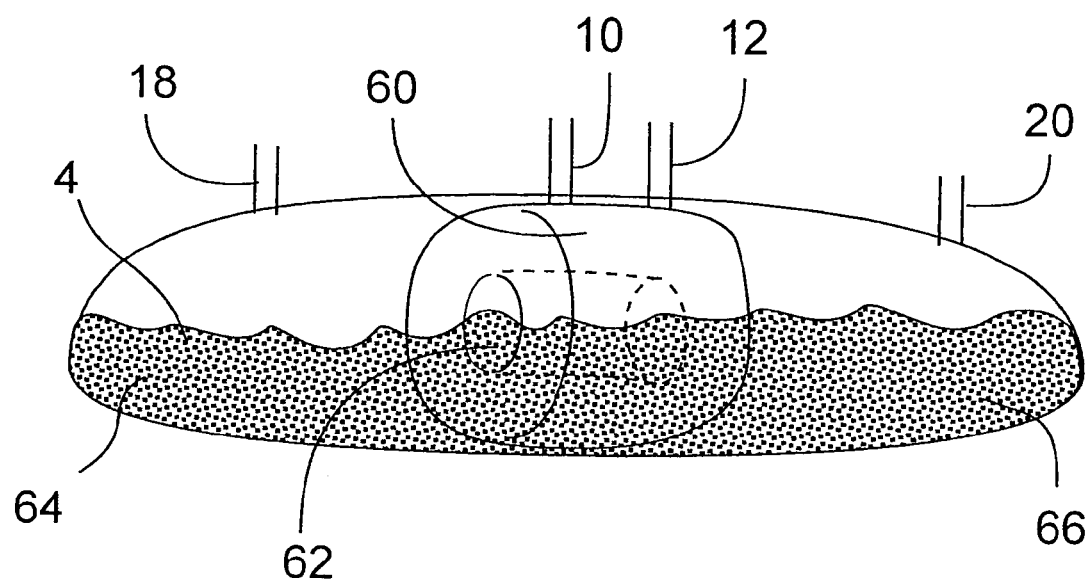
FIG. 10 shows another embodiment of the present invention in cross-sectional view.

FIG. 10 shows another embodiment in which the pressure bag 60 forms a central portion of the bag 2. A conduit 62 is formed through the bag 60 to provide fluid communication between the first section 64 of the bag 2 and the second portion 66. Preferably, the outer surface of the pressure bag 60 is permanently secured to the inner wall of the bag 2 so that the inflation/deflation tends to focus its movement toward the center of the bag 2. Fluid is moved between the portions 64 and 66 by the inflation/deflation of the pressure bag 60. Additionally, by using a narrowing restriction in the form of a conduit 62, one can achieve mixing of the fluid as it passes through the conduit. This can be enhanced through the use of vanes (not shown) in the conduit 62 so as to create a static mixer. Optionally, one or more additional pressure bags (not shown) similar to FIGS. 1-9 may be added to enhance fluid movement.

Figure 11:
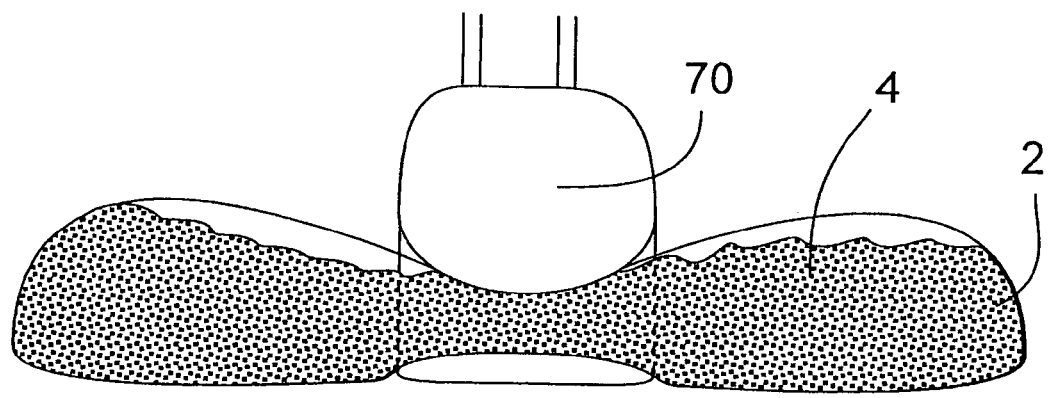
FIG. 11 shows another embodiment of the present invention in cross-sectional view.

FIG. 11 shows an additional embodiment of the present invention. Here, the pressure bag 70 surrounds a middle portion of the bag 2 and as it is inflated, pushes fluid 4 toward the ends. Upon deflation, the fluid 4 moves back toward the middle and opposite end. This embodiment creates a high degree of mixing and turbulence and is particularly useful in mixing application.

An additional use for the system of the present invention is as a pump or pressure regulated supply vessel for the liquid inside. If one wishes to pump the fluid inside the bag to another location, such as for storage or further processing, one can use the pressure bags and a valve on the exit of the bag to selectively push some, most or all of the fluid out of outlet of the bag. Likewise, where the fluid in the bag is to be filtered, one can use the pressure bags to create a constant pressure on the fluid inside the bag and to then supply that pressurized fluid from the bag through its outlet to an inlet of a filter. In this manner one eliminates the need for a pump in this disposable process. The pressure in the pressure bags as well as the fluid can be monitored and adjusted as needed to provide the correct pressure supply to the fluid as it is being filtered.

The bags used in the present invention can be those typically used in the biopharmaceutical industry for bioreactors, fermenters, storage bags and the like. Such bags are available from a variety of suppliers such as Stedim SA of France and Hyclone of Logan, Utah. These bags range in size from a few liters to 2000 liters or more. They typically are made from multiple layered (extruded or laminated) plastic film such as polyethylene, polypropylene, EVA copolymers, EVOH, PET, PETG, specialty or proprietary polymers such as the HyQ CX5-14 film available from Hyclone which is a coextruded multilayer film with an outer layer of elastomer with an EVOH barrier layer and an ultra-low density polyethylene product contact layer, blends of polymers and the like. The polymer(s) selected are chosen for the desired combination of cleanliness, strength and visibility.

The pressure bag(s) may be made of the same materials as the bags and can be made in the same way such as blow molding, heat sealing the seams of flat films together to form a bag and the like. When the pressure bags are used outside of the bag, the issue of cleanliness may be less of an issue. The key attributes of the outside pressure bags are strength, resiliency (to withstand the repeated inflation/deflation) and cost. If these bags are to be reused, one can consider the use of elastomeric materials such as rubbers (natural or synthetic [nitrile, neoprene and the like]), elastomers such as Styrene Butadiene Styrene copolymers (SBS copolymers), thermoplastic elastomers such as SANTOPRENE® resin available from Advanced Elastomer Systems of Akron, Ohio and the like. When used inside the bags and therefore in contact with the product, the pressure bags should be made of the same materials as the bags themselves in order to maintain cleanliness.

As described above, the pressure bags may be inflated with air, other gases or fluids. The medium chosen depends upon the user and the most common source available. Most factories have in-house air and vacuum lines and these are the ones that would most typically be used in this application.

Pressure regulators may be needed in some installations to maintain the pressure of the air to bags within a set desired range so as to avoid damage to the bag by overinflation or to prevent underinflation of the bag. The pressure used in a given bag will vary depending upon the strength of the bag, the amount of compression or movement of the bag desired and the available source of pressure. Typically, the pressure will be from about 5 psi to 100 psi, more typically from about 10 psi to about 80 psi.

If desired, the use of a vacuum on the outlet of the pressure bag may help in the rapid deflation of the bag when desired. While useful, it is not however necessary to the present invention. A simple pressure release valve is all that is necessary as the movement of the fluid in the bag from the end being inflated toward the end being deflated will add weight (of the moving fluid in the bag) against the deflating pressure bag to help in its deflation.

When a liquid such as water or hydraulic fluid is used, pumps may be used to supply the desired pressure and remove the desired amount of pressurized fluid from the pressure bags as needed. Any pump commonly used in the pharmaceutical or food industry may be used including piston pumps, rotary pumps, peristaltic pumps and the like.

The number of cycles of inflation/deflation per minute or hour depends upon the application involved. Some applications such as mixing will call for a near continuous movement of the liquid in the bag and therefore require one or more inflation/deflation cycles per minute. Often the bag inflation/deflation cycle can from one (1) to about thirty (30) cycles per minute in such applications. At the other extreme, where only a slight movement of the liquid is required or desired, the inflation/deflation cycle may be on the order of from about one (1) about sixty (60) cycles per hour. Other applications, such as for mixing of components which can withstand shear and/or foaming, the cycles may bee even faster than those described above if desired.

Additionally, the inflation/deflation cycle may be coupled with other functions of the bag such as nutrient supply or gas supply and the removal of exhaust gases, excrement and bioproducts. The timing of the introduction of gases, nutrients and the like can be made with the movement of the bag by the pressure bag such that the liquid movement creates a draw or pressure differential on the gas/nutrient inlet to the bag to help pull the desired amount into the bag as required. Likewise the pressure differential can work on the outlet to exhaust spent respiratory gases or to allow for the sampling of an aliquot of liquid for testing or removal of a portion of the liquid to remove excrement and the like.

Figure 12:
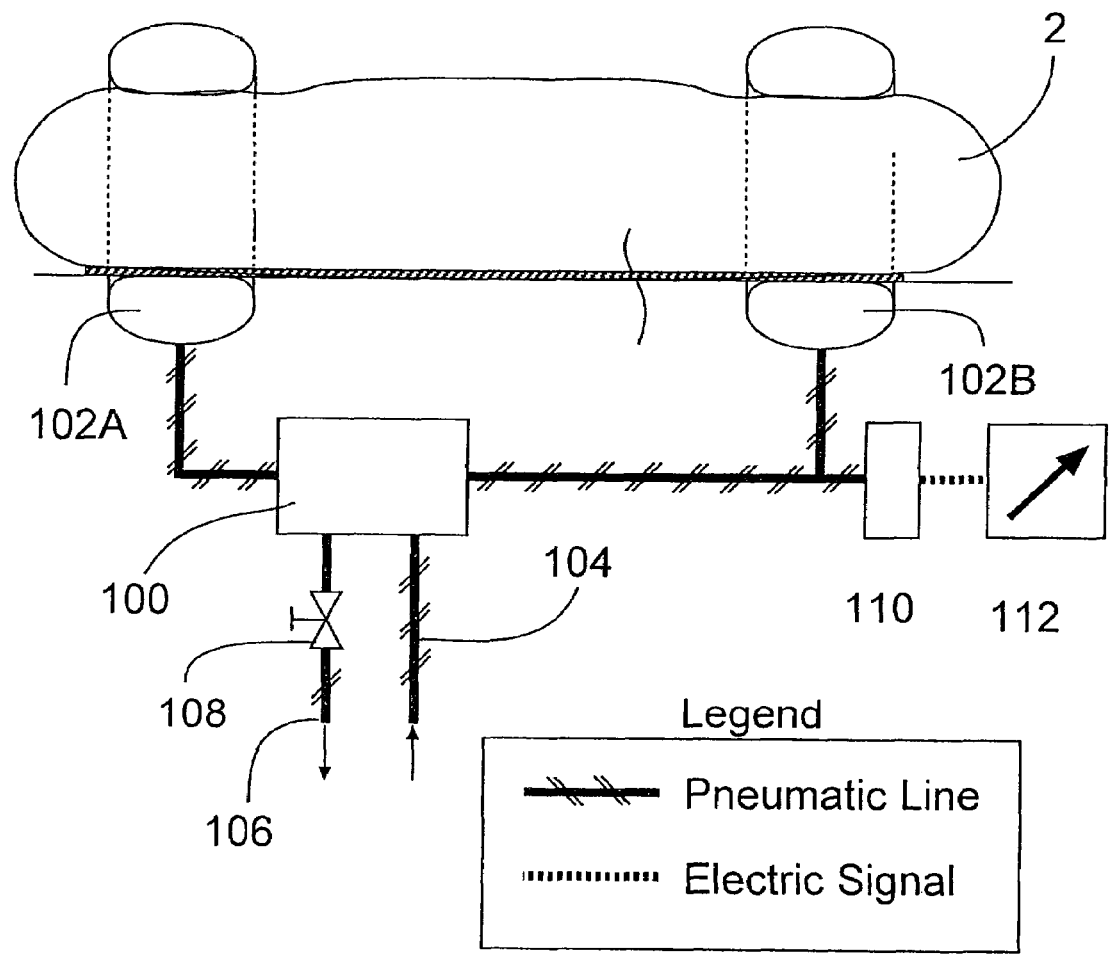
FIG. 12 shows a control unit for an embodiment of the present invention.

The inflation/deflation may be done manually or by automation. It is preferred that the system be automated to reduce labor costs and ensure repeated accuracy. One such system is shown in FIG. 12. Here a control unit 100 monitors a parameter of the pressure bags 102A and B such as time of inflation or deflation, pressure and the like. When the parameter in one bag, for example the pressure in 102B reaches a set lower level or zero, the control unit will stop inflating bag 102A, begin to fill bag 102B through pressure supply 104 and begin to deflate bag 102A through exhaust line 106 shown with the preferred exhaust valve 108. Also shown is pressure monitor 110 for the bags and a meter for displaying the number of cycles per a given time (be it minutes or hours). If desired the control unit may be a PID controller or a computer. Software may also be incorporated in to the system as desired to allow one greater flexibility and control.

The use of controllable valves, such as pneumatically controlled valves or solenoid valves on the inlets and outlets to the bags 102A and B allow the control unit 100 to work more effectively. However others means for controlling the inflation/deflation of the bags 102A and B are also contemplated. For example, one could use a simple slow release restrictor on the outlet of the bags 102A and B that deflates at a rate slower than the air supplied to the bag to allow it to inflate when desired. One simply switches air pressure from the inlet of one bag to the other based upon the rate of deflation of the restrictor, thereby controlling the inflation/deflation cycle in that manner.

The present invention is shown in several embodiments and others can be easily contemplated by those of ordinary skill in the art. It meant to include those embodiments as well in the description and claims of the present invention.

The present invention provides one with a simple system for moving liquid, even in large volumes in a disposable system. It allows one to achieve the adequate movement and/or mixing of components as desired without the need for capital and maintenance intensive equipment such as rocking tables or hydraulic hoists or cranes. It also takes advantage of common air/vacuum supplies in factories. While contemplated for use in the biopharmaceutical industry, it is clear that the device of the present invention has applications in other fields such as beer brewing, wine making, mixing of hazardous components, paints, epoxies and the like in disposable bags.

What I claim:

1. A mixing device consisting essentially of a mixing bag having an inner volume, the inner volume containing a liquid to mixed, one or more pressure bags being in a position selected from the group consisting of below and around the mixing bag, each of the one or more pressure bags having an inlet, each of the one or more pressure bags having an outlet, the inlet of the one or more pressure bags being connected to a source of pressurized gas and being capable of being selectively opened and closed so as to inflate and deflate the one or more pressure bags as desired.

2. The device of claim 1 wherein the one or more pressure bags are adjacent an outside portion of the mixing bag and are secured to the mixing bag.

3. The device of claim 1 wherein the one or more pressure bags are one in number and is adjacent an outside portion of the mixing bag at a central location.

4. The device of claim 1 wherein the inlet and/or outlet of each of the one or more pressure bags is selectively opened and closed through one or more valves adjacent the inlet and/or outlet of each of the one or more pressure bags.

5. A system for the mixing of components consisting essentially of a mixing bag having a volume for containing the components to be mixed, one or more components, at least one of the one or more components being in liquid form, the mixing bag having an inlet and an outlet, the inlet and outlet being capable of being selectively opened and closed, one or more pressure bags being positioned adjacent the mixing bag, the one or more pressure bags being in a position selected from the group consisting of below and around the mixing bag, each of the one or more pressure bags having an inlet, and each of the one or more pressure bags having an outlet, the inlet of the pressure bag being connected to a source of pressurized gas and a control unit connected to at least the pressure bag inlet to control the selective opening and closing of the inlet.

6. The system of claim 5 wherein each inlet to each of the one or more pressure bags has a valve actuated by the control unit to control the selective opening and closing of each inlet.

7. A method for the mixing of components consisting essentially of a mixing bag having an inner volume, the volume containing two or more constituents to be mixed, at least one of the two or more constituents being a liquid, providing one or more pressure bags positioned adjacent the mixing bag, the pressure bags being in a position selected from the group consisting of below and around the mixing bag, each of the one or more pressure bags having an inlet, each of the one or more pressure bags having an outlet, the inlet and outlet being capable of being selectively opened and closed, the inlet of the one or more pressure bags being connected to a source of pressurized gas, closing the outlet to at least one of the one or more pressure bags and selectively applying the pressurized gas to the inlet of at least one of the one or more pressure bags so as to inflate at least one of the one or more pressure bags, selectively stopping the supply of pressurized gas to the at least one of the one or more pressure bags by closing the inlet of the at least one of the one or more pressure bags to create a wave motion of the constituents within the volume and opening the outlet to at least one of the one or more pressure bags to deflate the at least one of the one or more pressure bags.

8. A mixing device consisting essentially of a mixing bag having an inner volume, the inner volume containing a liquid to mixed, the mixing bag having a first end, a second end and a middle, one or more pressure bags positioned adjacent the first end of the mixing bag, the one or more pressure bags being in a position selected from the group consisting of below and around the mixing bag, each of the one or more pressure bags having an inlet, and each of the one or more pressure bags having an outlet, the inlet and outlet being capable of being selectively opened and closed, the inlet of the one or more pressure bags being connected to a source of pressurized gas and being capable of being selectively opened and closed so as to inflate and deflate the one or more pressure bags as desired.

9. The device of claim 8 wherein there is one pressure bag, it is located at the first end of the mixing bag and it is in a position below the mixing bag.

10. The device of claim 8 wherein there is one pressure bag, it is located at the middle of the mixing bag and it is in a position around the mixing bag.

* * * * *